United States Patent
Buscemi et al.

(10) Patent No.: US 8,381,735 B2
(45) Date of Patent: Feb. 26, 2013

(54) TONGUE IMPLANT

(75) Inventors: Paul J. Buscemi, Medina, MN (US);
Kurt D. Krueger, Stacy, MN (US);
Paula Bushendorf, Woodbury, MN (US)

(73) Assignee: Medtronic Xomed, Inc., Jacksonville, FL (US)

(*) Notice: Subject to any disclaimer, the term of this patent is extended or adjusted under 35 U.S.C. 154(b) by 239 days.

(21) Appl. No.: 12/586,170

(22) Filed: Sep. 16, 2009

(65) Prior Publication Data
US 2010/0059066 A1   Mar. 11, 2010

Related U.S. Application Data

(63) Continuation of application No. 11/706,729, filed on Feb. 15, 2007, now abandoned, which is a continuation-in-part of application No. 11/542,455, filed on Oct. 3, 2006, now abandoned.

(51) Int. Cl.
*A61F 5/56* (2006.01)

(52) U.S. Cl. .......................... 128/848; 128/897; 128/898

(58) Field of Classification Search .................. 128/848, 128/859–862; 602/902; 623/9, 11.11, 14.11
See application file for complete search history.

(56) References Cited

U.S. PATENT DOCUMENTS

| | | | |
|---|---|---|---|
| 4,193,137 A | 3/1980 | Heck | |
| 4,347,847 A | 9/1982 | Usher | |
| 4,655,771 A | 4/1987 | Wallsten | |
| 4,672,673 A | 6/1987 | Katz | |
| 5,258,000 A | 11/1993 | Gianturco | |
| 5,522,896 A | 6/1996 | Prescott | |
| 5,578,086 A | 11/1996 | Prescott | |
| 5,843,021 A | 12/1998 | Edwards et al. | |
| 5,988,171 A | 11/1999 | Sohn et al. | |
| 6,161,541 A | 12/2000 | Woodson | |
| 6,250,307 B1 | 6/2001 | Conrad et al. | |
| 6,401,717 B1 | 6/2002 | Conrad et al. | |
| 6,413,254 B1 | 7/2002 | Hissong | |
| 6,431,174 B1 | 8/2002 | Knudson et al. | |
| 6,513,530 B2 | 2/2003 | Knudson et al. | |
| 6,523,541 B2 | 2/2003 | Knudson | |

(Continued)

FOREIGN PATENT DOCUMENTS

| | | |
|---|---|---|
| DE | 199 20 114 A1 | 11/2000 |
| EP | 1039859 B1 | 12/1998 |

(Continued)

OTHER PUBLICATIONS

Eisele et al., "Direct Hypoglossal Nerve Stimulation in Obstructive Sleep Apnea", *Arch. Otolaryngol. Head Neck Surg.*, vol. 123, pp. 57-61 (1997).

(Continued)

*Primary Examiner* — Patricia Bianco
*Assistant Examiner* — Camtu Nguyen
(74) *Attorney, Agent, or Firm* — Merchant & Gould, P.C.

(57) ABSTRACT

A patient's obstructive sleep apnea is treated by identifying a patient with sleep apnea attributable at least in part to movement of a base of a tongue of the patient toward a pharyngeal wall of the patient. The tongue is stiffened by an implant sized to be placed within the tongue. A distal portion of the implant is sized to extend within the tongue from a first end near a mandibular-geniohyoid interface to a second end near a base of the tongue. A proximal portion is attached to the first end and adapted to be secured to a jaw bone of the patient following a period of healing after placement of the implant in the tongue.

16 Claims, 9 Drawing Sheets

U.S. PATENT DOCUMENTS

| | | |
|---|---|---|
| 6,523,542 B2 | 2/2003 | Knudson et al. |
| 6,601,584 B2 | 8/2003 | Knudson et al. |
| 6,736,823 B2 | 5/2004 | Darois |
| 6,918,396 B1 | 7/2005 | Badylak |
| 6,955,172 B2 | 10/2005 | Nelson |
| 6,997,956 B2 | 2/2006 | Cauthen |
| 7,048,753 B2 | 5/2006 | Shalaby |
| 7,073,505 B2 | 7/2006 | Nelson |
| 7,078,378 B1 | 7/2006 | Owen et al. |
| 7,081,086 B2 | 7/2006 | Lau et al. |
| 2002/0083820 A1 | 7/2002 | Greenhalgh |
| 2004/0020492 A1 | 2/2004 | Dubrul et al. |
| 2004/0028676 A1 | 2/2004 | Klein et al. |
| 2004/0045556 A1 | 3/2004 | Nelson et al. |
| 2004/0134491 A1 | 7/2004 | Pflueger et al. |
| 2004/0139975 A1 | 7/2004 | Nelson et al. |
| 2004/0149290 A1 | 8/2004 | Nelson et al. |
| 2005/0004417 A1 | 1/2005 | Nelson et al. |
| 2005/0092332 A1 | 5/2005 | Conrad et al. |
| 2005/0092334 A1 | 5/2005 | Conrad et al. |
| 2005/0126563 A1 | 6/2005 | van der Burg et al. |
| 2005/0142163 A1 | 6/2005 | Hunter et al. |
| 2005/0154412 A1 | 7/2005 | Krueger et al. |
| 2005/0199248 A1 | 9/2005 | Pflueger et al. |
| 2005/0267321 A1 | 12/2005 | Shadduck |
| 2005/0281883 A1 | 12/2005 | Daniloff et al. |
| 2006/0029591 A1 | 2/2006 | Vukicevic et al. |
| 2006/0070626 A1 | 4/2006 | Frazier et al. |
| 2006/0153816 A1 | 7/2006 | Brown et al. |
| 2006/0157055 A1 | 7/2006 | Pflueger et al. |
| 2006/0235264 A1 | 10/2006 | Vassallo |
| 2006/0235380 A1 | 10/2006 | Vassallo |
| 2007/0190490 A1 * | 8/2007 | Giorno .................. 433/173 |

FOREIGN PATENT DOCUMENTS

| | | |
|---|---|---|
| GB | 2 355 936 A | 5/2001 |
| WO | WO 2006/012188 A1 | 2/2006 |
| WO | WO 2006/072571 A1 | 7/2006 |

OTHER PUBLICATIONS

Miller et al., "Role of the tongue base suspension suture with The Repose System bone screw in the multilevel surgical management of obstructive sleep apnea", *Otolaryngol. Head Neck Surg.*, vol. 126, pp. 392-398 (2002).

Powell et al., "Radiofrequency tongue base reduction in sleep-disordered breathing: A pilot study", *Otolaryngol. Head Neck Surg.*, vol. 120, pp. 656-664 (1999).

Powell et al., "Radiofrequency Volumetric Reduction of the Tongue—A Porcine Pilot Study for the Treatment of Obstructive Sleep Apnea Syndrome", *Chest*, vol. 111, pp. 1348-1355 (1997).

* cited by examiner

TONGUE IMPLANT

CROSS-REFERENCE TO RELATED APPLICATION

The present application is a continuation of U.S. patent application Ser. No. 11/706,729, filed Feb. 15, 2007, now abandoned; which is a continuation-in-part of U.S. patent application Ser. No. 11/542,455, filed Oct. 3, 2006, now abandoned; which applications are hereby incorporated by reference in their entirety.

BACKGROUND OF THE INVENTION

1. Field of the Invention

This invention pertains to a method for treating a condition of an upper airway of a patient. More particularly, this invention is directed to a method for treating obstructive sleep apnea by stiffening a tongue of a patient.

2. Description of the Prior Art

Upper airway conditions such as obstructive sleep apnea ("OSA") and snoring have received a great deal of attention. These conditions have recognized sociological and health implications for both the patient and the patient's bed partner.

Numerous attempts have been made towards treating OSA and snoring. These include placing implants in either the tissue of the soft palate or the pharyngeal airway as disclosed in commonly assigned U.S. Pat. No. 6,250,307 to Conrad et al. dated Jun. 26, 2003, U.S. Pat. No. 6,523,542 to Metzger et al. dated Feb. 25, 2003 and U.S. Pat. No. 6,431,174 to Knudson et al. dated Aug. 13, 2002. Further, U.S. Pat. No. 6,601,584 to Knudson et al. dated Aug. 5, 2003 teaches a contracting implant for placement in the soft palate of the patient.

Another prior art technique for treating OSA or snoring is disclosed in U.S. Pat. No. 5,988,171 to Sohn et al. dated Nov. 23, 1999. In the '171 patent, a cord (e.g., a suture material) (element 32 in FIG. 6 of the '171 patent) is placed surrounding a base of the tongue and secured to the jaw by reason at an attachment member (element 20 in FIG. 6 of the '171 patent). In the method of the '171 patent, the member 32 can be shortened to draw the base of the tongue toward the jaw and thereby move the tissue of the base of the tongue away from the opposing tissue of the pharyngeal airway. However, this procedure is often uncomfortable. This procedure, referred to as tongue suspension, is also described in Miller et al., "Role of the tongue base suspension suture with The Repose System bone screw in the multilevel surgical management of obstructive sleep apnea", Otolaryngol. Head Neck Surg., Vol. 126, pp. 392-398 (2002).

Another technique includes debulking tissue by applying radio frequency ablation to either the tongue base or of the soft palate to debulk the tissue of the tongue or palate, respectively. This technique is illustrated in U.S. Pat. No. 5,843,021 to Edwards et al. dated Dec. 1, 1998. RF tongue base reduction procedures are described in Powell et al., "Radiofrequency tongue base reduction in sleep-disordered breathing: A pilot study", Otolaryngol. Head Neck Surg., Vol. 120, pp. 656-664 (1999) and Powell et al., "Radiofrequency Volumetric Reduction of the Tongue—A Porcine Pilot Study for the Treatment of Obstructive Sleep Apnea Syndrome", Chest, Vol. 111, pp. 1348-1355 (1997).

A surgical hyoid expansion to treat OSA is disclosed in U.S. Pat. No. 6,161,541 to Woodson dated Dec. 19, 2000. Other tongue treatments for OSA include stimulation of the hypoglossal nerve. This procedure is described in Eisle et al., "Direct Hypoglossal Nerve Stimulation in Obstructive Sleep Apnea", Arch. Otolaryngol. Head Neck Surg., Vol. 123, pp. 57-61 (1997).

Commonly assigned U.S. patent application Publication Nos. US 2005/0092332 A1 and US 2005/0092334 A1 (both published May 5, 2005) describe tongue-based treatments to treat obstructive sleep apnea. U.S. patent application Ser. Nos. 11/107,160 and 11/107,161 (both filed Apr. 15, 2005 and assigned to the assignee of the present invention) describe various implants for a tongue to treat obstructive sleep apnea.

European Patent EP 1,039,859 B1 granted Dec. 3, 2003 describes a brace placed in the tongue. German Patent No. 19 920 114 describes struts in pharyngeal wall. U.S. patent application Publication Nos. US 2005/0126563 A1 published Jun. 16, 2005 and US 2005/0199248 A1 published Sep. 15, 2005 describe stents in an airway. U.S. patent application Publication Nos. US 2004/0139975 published Jul. 22, 2004 and US 2004/0149290 published Aug. 5, 2005 (both assigned to Apneon Inc.) describe struts or magnets in the tongue.

SUMMARY OF THE INVENTION

According to a preferred embodiment, obstructive sleep apnea of a patient is treated by identifying a patient with sleep apnea attributable at least in part to movement of a base of a tongue of said patient toward a pharyngeal wall of said patient. The method includes identifying a region in the tongue extending from a mandibular-geniohyoid interface to the base of the tongue and stiffening a tissue of the tongue throughout the identified region. The region is stiffened by an implant sized to be placed within a tongue of the patient. A distal portion of the implant is sized to extend within the tongue from a first end near a mandibular-geniohyoid interface to a second end near a base of the tongue. The proximal portion is attached to the first end and adapted to be secured to a jaw bone of the patient following a period of healing after placement of the implant in the tongue. In a most preferred embodiment, at least a portion of the proximal portion is formed of an elastomeric material for the implant to stretch and contract in response to movement of the tongue during speech and swallowing.

DESCRIPTION OF THE PREFERRED EMBODIMENT

With reference now to the various drawing figures in which identical elements are numbered identically throughout, a description of the preferred embodiment of the present invention will now be provided.

1. Disclosure of Parent Application

Figure 1:
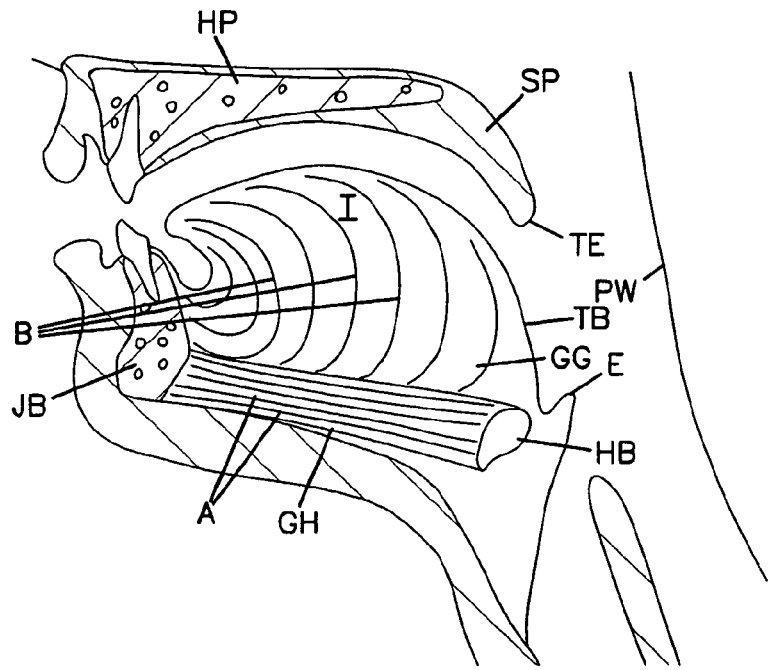
FIG. 1 is a side sectional schematic view of an upper airway of a patient and illustrating various anatomical features.

FIG. 1 is a schematic representation of an upper airway of a patient. FIG. 1 shows the tongue T with a tongue base TB opposing a pharyngeal wall PW. The hard palate HP and soft palate SP reside over the top of tongue T with the soft palate SP extending rearward to a trailing end TE between the tongue base TB and the pharyngeal wall PW.

A hyoid bone HB resides near the bottom of the tongue near an epiglottis E. A mandible or jaw bone JB is at the front of the tongue T. The geniohyoid muscle GH extends between the jaw bone JB and the hyoid bone HB at the bottom of the tongue T. The lines A of FIG. 1 illustrate the direction of muscle fibers in the geniohyoid muscle GH. The genioglossus muscle GG resides above the geniohyoid muscle GH. The genioglossus muscle GG has muscle fibers B which extend from the jaw bone JB and curve to radiate toward the surface of the tongue T.

When reclining during sleep, the tongue base TB may, in response to gravity or airflow, drop down in closer approximation to the pharyngeal wall PW. During sleep, the muscles of the tongue T (principally the genioglossus muscle GG) can stretch permitting the tongue T to fall back toward the pharyngeal wall PW.

The present invention is directed towards method and apparatus for stiffening the muscles of the tongue T in a manner to preclude the tongue T from falling toward the pharyngeal wall PW while avoiding interference with normal functions of the tongue T during speech and eating.

Figure 2:
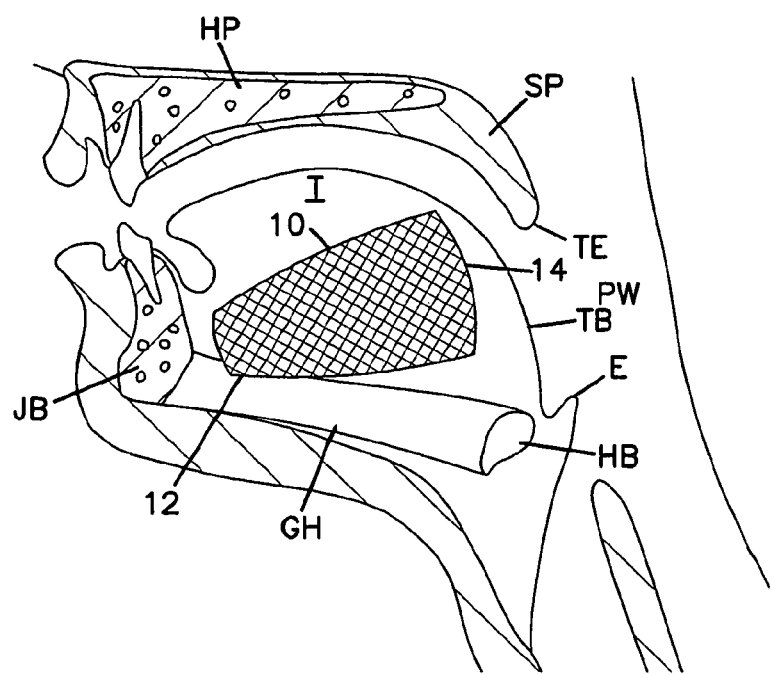
FIG. 2 is the view of FIG. 1 showing an implant of the present invention placed within the tongue according to a treatment method of the present invention.
Figure 4:
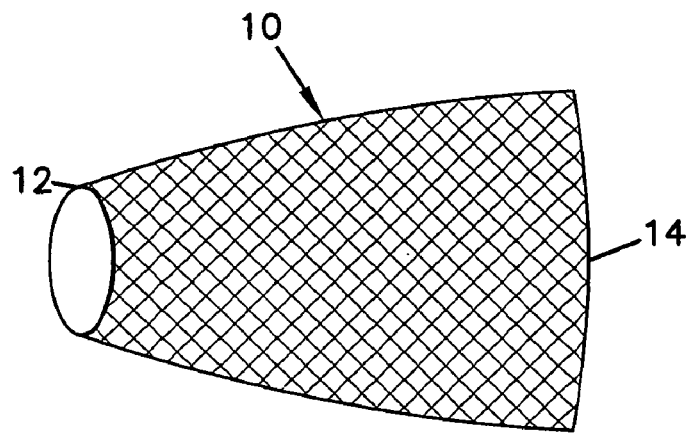
FIG. 4 is a perspective view of the implant of FIG. 3.

FIG. 2 illustrates the present invention as an implant 10 placed within the interior of the tongue T. The implant 10 has a proximal end 12 and a distal end 14. In a preferred embodiment, the implant 10 is a substantially planar sheet formed as a generally conical envelope best illustrated in FIG. 4. The distal end 14 is the base of a cone with opposing edges of the base being stitched or otherwise bonded together so that the interior of the implant 10 is accessible only through the proximal end 12. The implant 10 is a flat sheet with opposing surfaces of the cone compressed against one another.

Figure 3:
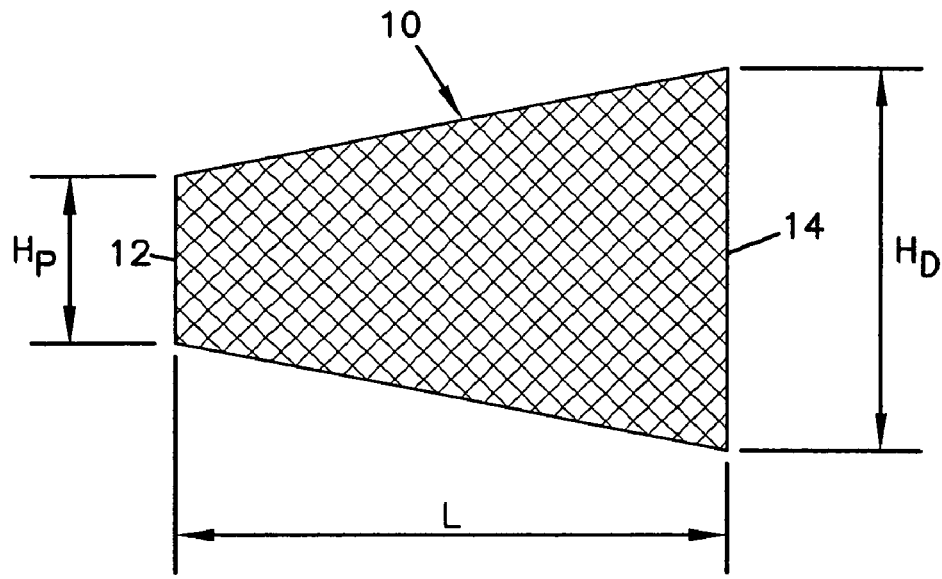
FIG. 3 is a side elevation view of the implant of FIG. 1.

The implant 10 is sized to be received within the tongue T with the proximal end 12 positioned in a region of the tongue T adjacent the interface of the jaw JB and geniohyoid muscle GH. The height of the proximal end 12 (illustrated as $H_P$ in FIG. 3) is sized for the proximal end 12 to be received within the tongue T at the juncture of the jaw bone JB and the geniohyoid muscle GH. The implant 10 is further sized to have a length L for the distal end 14 to be positioned adjacent the tongue base TB in close proximity to the tongue base TB when the proximal end 12 is positioned in a region of the tongue T adjacent the interface of the jaw JB and geniohyoid muscle GH. The height of the distal end 14 (illustrated as $H_D$ in FIG. 3) is sized for the distal end 14 to extend within the tongue base TB substantially covering a region of the tongue base TB opposing the pharyngeal wall PW between the epiglottis E and the trailing end TE of the soft palate TB. By way of non-limiting example, representative dimensions for $H_P$, $H_D$ and L are 1.0 centimeter, 2.5 centimeters and 4 centimeters, respectively. The fibrils of the material of implant 10 are about 20 microns to 100 microns in diameter. Depending on the braid or weave and the fibril diameter, the thickness of a sheet of the material may range from 50 to 500 microns. A double thickness TH (FIG. 12) (which is transverse to the anterior-posterior axis of the tongue T following implantation) would be about 100 to 1000 microns.

The material of the implant 10 is selected to produce a fibrotic response from the tissue of the tongue T following implantation of the implant 10 within the tongue T. The specific materials and construction may be varied to alter the degree of fibrotic response resulting from such implantation. By way of non-limiting example, the material of the implant 10 may be a knit or woven polyester or polypropylene material known to result in a fibrosis formation following implantation.

Figure 5:
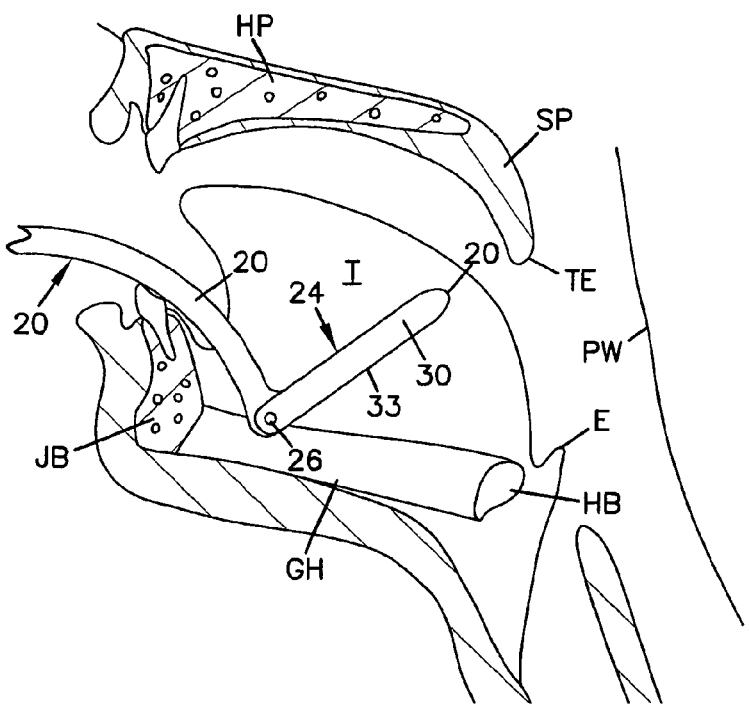
FIG. 5 is the view of FIG. 1 showing an incision formation tool placed within the tongue.

FIGS. 5-10 illustrate a technique and tools for placement of the implant 10 within the tongue. In FIG. 5, a tool 20 is shown for forming an incision in the tongue T sized to receive the implant 10. The tool 20 includes a curved handle 22 and a scissors end 24. The scissors end 24 is hinged to the handle at hinge point 26 and includes a pair of scissor blades 28, 30 (shown in FIG. 6). The tips 29, 31 of the blades 30, 28 are sharp to permit insertion of the tips 29, 31 through tissue into the tongue T. Further, the edges 27, 33 of the blades 28, 30 are sharp to permit slicing action of the scissor blades 28, 30 through tissue.

In use, the blades 28, 30 are collapsed so that they are in parallel alignment as shown in FIG. 5. The tips 31, 29 are passed through the patient's open mouth and are inserted into the tongue T at the front lower extremity of the tongue T just behind the jaw bone JB. Insertion is first made by urging the tips 29, 31 downwardly into the region of interface between the geniohyoid muscle GH and the jaw bone JB and then curving the direction of travel upwardly to urge the tips 29, 31 toward the tongue base TB.

Figure 6:
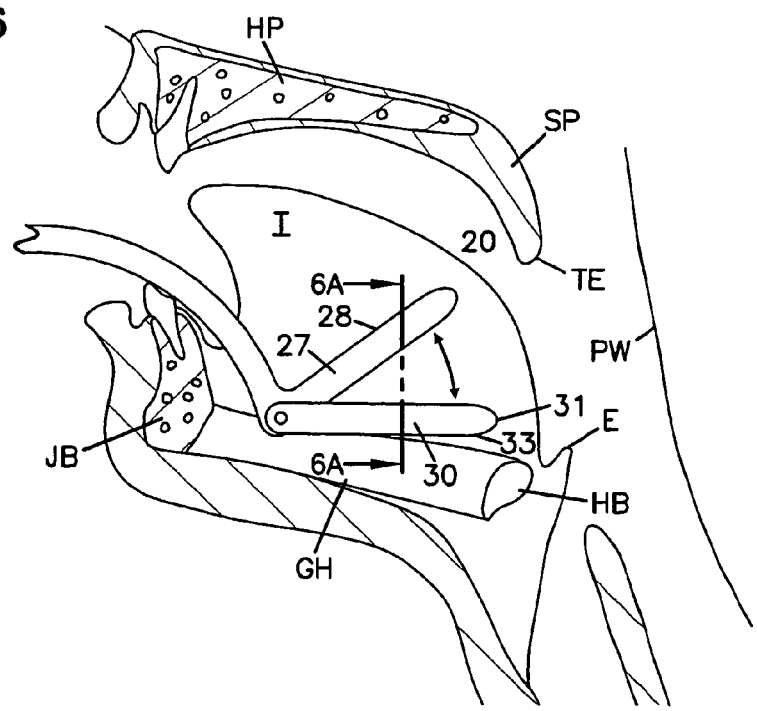
FIG. 6 is the view of FIG. 5 with the incision formation tool actuated to an open position to form a pocket for receiving the implant of FIG. 3.
Figure 6A:
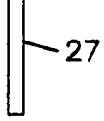
FIG. 6A is a view taken along line 6A-6A in FIG. 6.
Figure 6A:
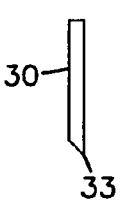

When the tool 20 is in the position of FIG. 5, the scissor blades 28, 30 are opened as shown in FIG. 6 to cut a pocket for receiving an implant 10. The tool 20 is then removed. The arcuate nature of the handle 22 permits formation of an incision pocket extending from the geniohyoid muscle GH at the jaw JB toward the tongue base TB between the epiglottis E and the trailing end TE of the soft palate SP.

Figure 7:
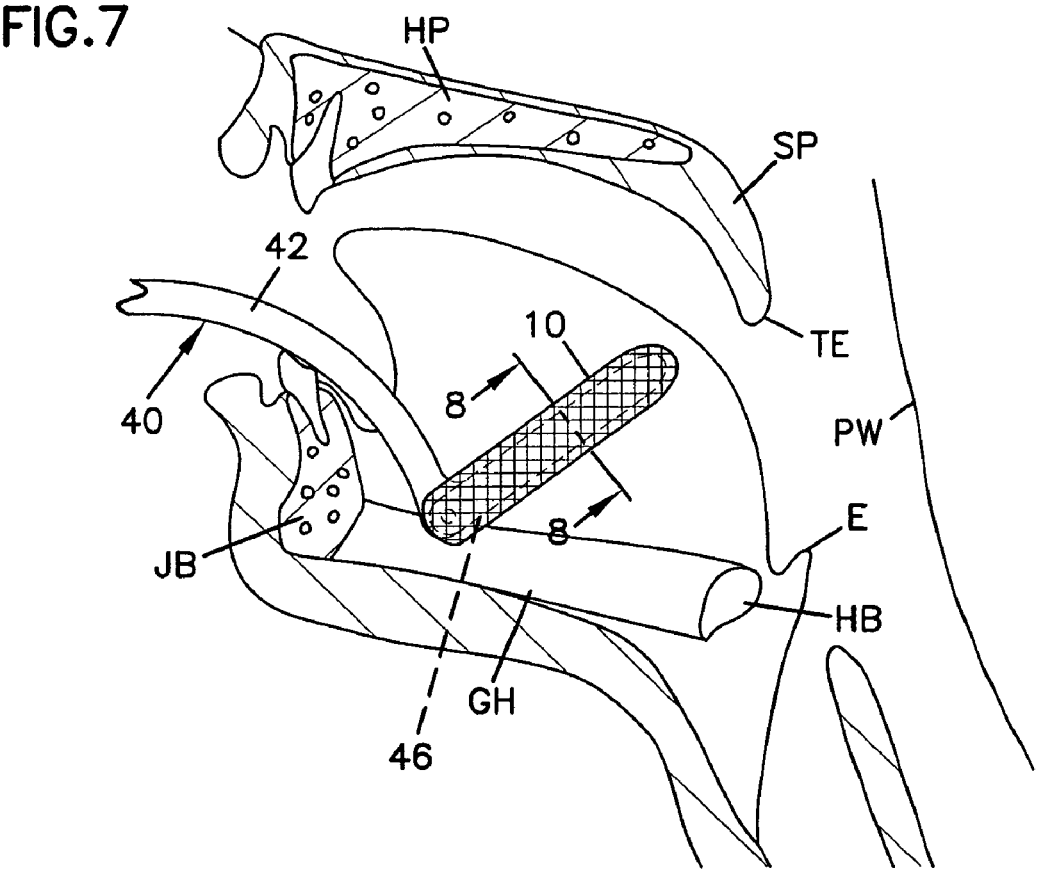
FIG. 7 is the implant of FIG. 3 disposed on an implant insertion tool before final deployment.

Following formation of the pocket, an insertion tool 40 is provided as illustrated in FIG. 7. Insertion tool 40 is similar in construction to the incision formation tool 20. It includes a curved handle 42 and scissor action blades 44, 46. Unlike blades 28, 30, the blades 44, 46 do not have knife edges in order to avoid damage to the implant 10.

Figure 8:
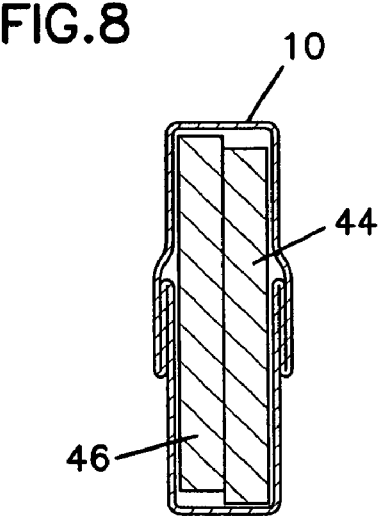
FIG. 8 is a view taken along line 8-8 of FIG. 7.
Figure 9:
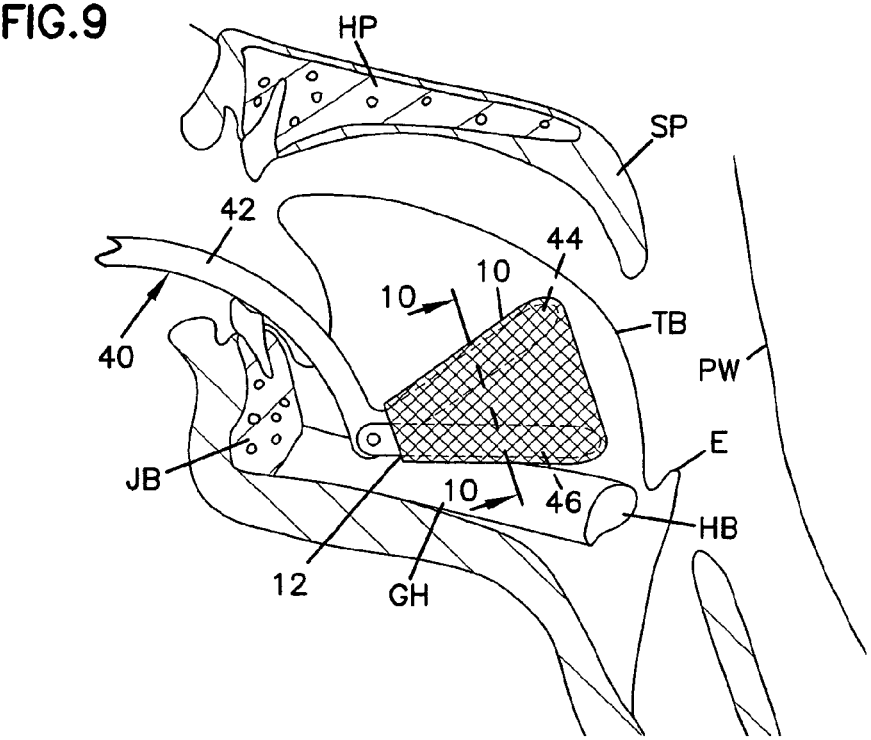
FIG. 9 is the view of FIG. 7 with the implant insertion tool moved to an open position to fully place the implant within a pocket formed within the tongue.
Figure 10:
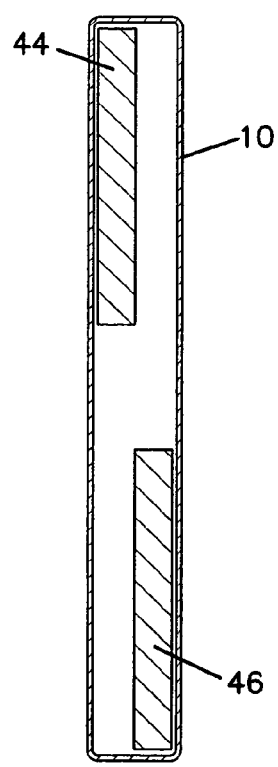
FIG. 10 is the view taken alone line 10-10 of FIG. 9.

With the blades 44, 46 in parallel alignment as shown in FIGS. 7 and 8, the tips of the blades 44, 46 are inserted into the interior of the implant 10 through the proximal end 12. The implant 10 can then be folded surrounding the blades 44, 46 into a compact configuration surrounding the blades 44, 46 as shown in FIGS. 7 and 8. The tool 40 carrying the implant 10 is placed into the incision pocket formed by tool 20. Such positioning is shown in FIG. 7. After such positioning, the blades 44, 46 are actuated to an open position shown in FIG. 9 urging the implant 10 to its expanded state. The blades 44, 46 can then be returned to their collapsed state and removed from the tongue T leaving the implant 10 in desired position within the tongue T. Referring to FIG. 10, in the expanded state, the implant has a substantially planar sheet construction as defined by the width of the opened blades 44, 46 of the insertion tool 40. In contrast and as will be described in greater detail hereinafter, other implant embodiments may have a tubular construction.

As mentioned, it is desired that the proximal end 12 of the implant 10 be as positioned as close as possible to the jaw bone JB in the region of the geniohyoid muscle GH. If necessary, the surgeon can form additional incisions through the tongue T to pull the proximal end 12 into the geniohyoid muscle GH in close proximity to the jaw bone JB.

Figure 11:
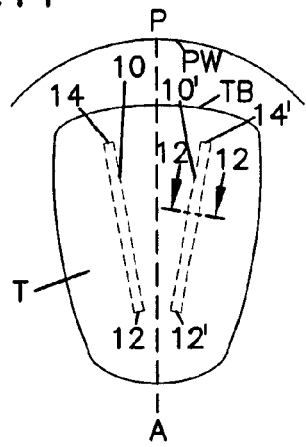
FIG. 11 is the top plan view of a tongue showing positioning of two implants within the tongue.

FIG. 11 shows two implants 10, 10' positioned within the tongue T in the manner such as that previously described. Ideally, the implants 10, 10' extend along the anterior posterior A-P axis. The proximal ends 12, 12' are positioned in close approximation to the anterior-posterior axis A-P. Preferably, the implants 10, 10' do not extend straight back. Instead, they are angled outwardly toward the sides of the tongue T. As a result, the distal ends 14, 14' are spaced apart at opposite lateral extremities of the tongue base TB.

Figure 12:
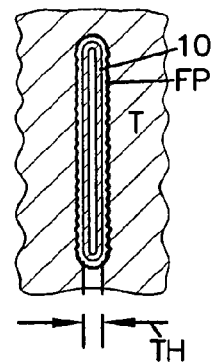
FIG. 12 is a view taken along line 12-12 of FIG. 11.

Following implantation, a fibrotic capsule FC forms around the material of the implant 10. The capsule FC is illustrated in FIG. 12. The fibrotic capsule FC adds stiffness to the tissue of the tongue T.

At the juncture of the geniohyoid muscle GH and the jaw bone JB (referred to herein as the "mandibular-geniohyoid interface", muscle fibers of the tongue are tendon-like. By "tendon-like", it is meant the muscle fibers are less susceptible to stretching than the remainder of the length of the fibers. Since the fibrotic capsule FC and the proximal end 12 of the implant 10 originate in this region, a substantially non-stretchable region is formed in the tongue T by reason of the fibrotic capsule FC and the implant 10.

In the absence of an implant 10, substantially the entire length of muscle fibers from the jaw bone JB to the tongue base TB can stretch during sleep resulting in the tongue base TB falling against the soft palate SP or pharyngeal wall PW during sleep. With the implant 10 extending from the jaw bone JB to the tongue base TB, the muscle fibers in contact with the implant 10 and resulting fibrotic capsule FC are much less susceptible to stretching.

Use of two implants 10, 10' (FIG. 11) forms two such non-stretchable planes within the tongue T. The placement of FIG. 11 ties the tongue base TB to the jaw bone JB with the lateral extremities of the tongue based TB being treated to resist stretching. If desired, a third implant could be placed along the anterior-posterior axis A-P to further resist tongue stretching.

Figure 13:
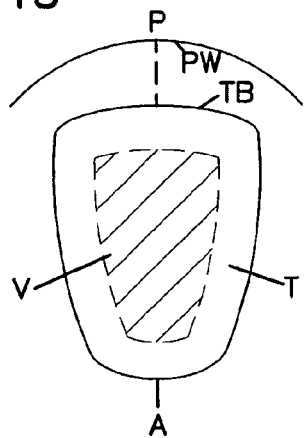
FIG. 13 is a top plan view of a tongue showing an entire target region being stiffened.
Figure 14:
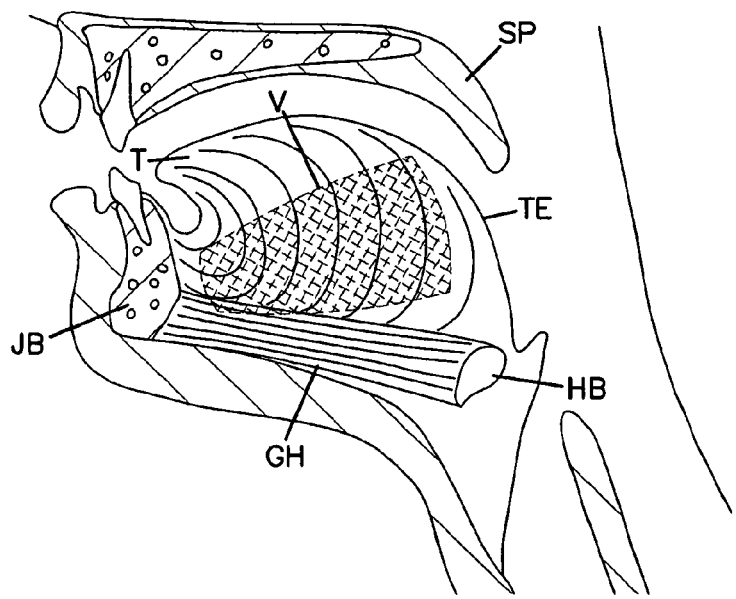
FIG. 14 is the view of FIG. 1 showing the entire target region of FIG. 13.

FIGS. 13 and 14 illustrate extreme treatments where the entire volume of the tongue from the mandibular-geniohyoid interface to the base of the tongue is stiffened. This volume V is illustrated in FIGS. 13 and 14 as a shaded area. The volume is defined as a generally conical volume having an apex at the mandibular-geniohyoid interface. The base of the conical volume is at the tongue base TB near the surface of the tongue and covering the portion of the tongue base TB opposing the pharyngeal wall PW between the epiglottis E and the training end TE of the soft palate SP. The volume V extends between the lateral extremities of the tongue base TB.

Treatment of the entire volume can be accomplished by multiple implants 10 placed as described above. Alternatively, the volume V can be injected with any fibrosis-inducing agent (e.g., microbeads) throughout the volume V.

Ideally, the implant 10 will contract and expand with the muscle as it heals. Otherwise, a capsule surrounding the implant 10 will form as muscle slides over the implant 10. This property is enabled by a combination of factors: the restoring force of the implant 10, the friction against the tissue and attachments if any at either end. The mesh material of the implant 10 aids in achieving these objectives. The goal is to have an appropriate amount of spring tension/expansion and wall friction/in-growth such that the implant 10 contracts and expands with tissue. It is desirable to avoid an implant so stiff as to overly contract the muscle. This may cause the distal end of the implant to slide more proximal. As the scar forms and contracts, the implant contracts more permanently with the scar. This suggests the restoring force decreases over time. Biodegradable fibers suitable for this purpose or biodegradable coatings on the fibers themselves (which adhere the fibers together) may be used. The elastic properties of the implant should are approximately between 5 kPa to 50 kPa. The frictional force should be approximately 2N to 4 N. The patient's physiology and the size of the implant affect the range for these values.

FIGS. 15-18 illustrate an alternative embodiment in which the target area or volume of the tongue is stiffened by placement of a plurality of tubular implants 10". One such implant 10" is separately shown in FIGS. 16 and 16A. In a representative embodiment, the implant 10" is tube of polyester or other material selected to induce fibrosis following implantation in the tongue T. The implant 10" has a length L' of 3-5 centimeters, an outside diameter $D_O$ of about 1 mm to 3 mm and an inside diameter $D_I$ resulting from a wall thickness of about 50 to 500 microns. Implants 10" for a single patient need not all be the same length L'. More interior implanted tubes 10" may be shorter so that proximal ends 12" do not impinge upon one another when multiple implants 10" are used (as will be described).

Figure 15:
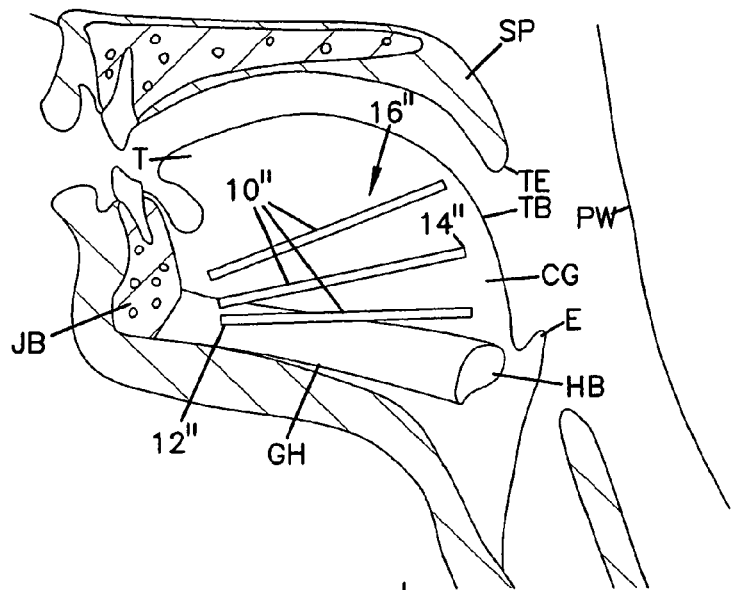
FIG. 15 is the view of FIG. 2 showing an alternative embodiment of an implant according to the present invention showing multiple implants in the tongue.
Figure 16:
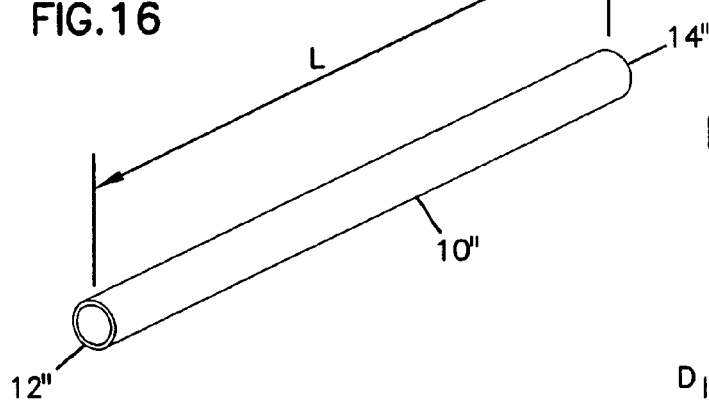
FIG. 16 is a perspective view of a tubular implant used in the embodiment of FIG. 15.
Figure 16A:
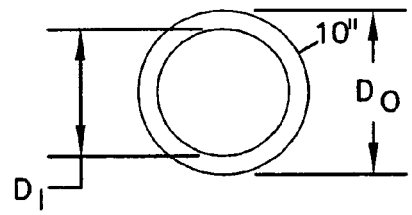
FIG. 16A is an end elevation view of the implant of FIG. 16.
Figure 17:
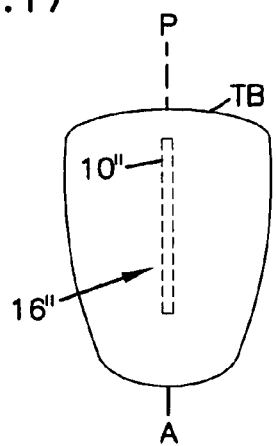
FIG. 17 is a top plant view of a tongue with implants of FIG. 16 arranged extending along an anterior-posterior axis of the tongue.
Figure 18:
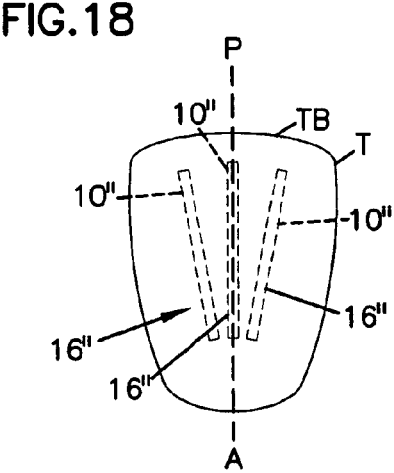
FIG. 18 is the view of FIG. 17 with the implants disposed in the target region of FIG. 13.

The implant 10" may be placed with a proximal end 12" at the mandibular-geniohyoid interface and with a distal end 14" at the tongue base TB. FIG. 15 shows three such implants 10" disposed in a vertical planar array 16" substantially filling the plane of implant 10 of FIG. 2. A single such array 16" may be positioned in line with the anterior posterior axis A-P (as shown in FIG. 17) or multiple such arrays 16" may be positioned similar to the positioning of implants 10 in FIG. 11 (as illustrated in FIG. 18). Use of tubular implant 10" permits a more uniform distribution of implants in the target volume V and creation of a filled target volume of more conical shape.

The insertion tool for the tube shaped implants 10" may be much like the insertion tool described in U.S. patent application Publication No. 2005/0154412 A1 (incorporated herein by reference) which describes a tool for placing a solid braided implant such as that marketed by assignee of the present application (Restore Medical Inc., St. Paul, Minn., USA) under the trademark "Pillar". The tool may be modified to replace the needle of the tool with a rod received within the implant 10″ through the proximal end 12″. The rod may extend to the distal tip 14″ of the implant 10″. Retracting the rod leaves the implant 10″ in desired position in the tongue T.

In the foregoing example, no stiffening treatment is made in the tongue T in the upper region of the tongue T. Generally defined herein as the region of the tongue T above and forward of a line from the jaw bone JB to the trailing end of the hard palate HP, this region of the tongue T is active in speech and swallowing. Since no treatment is made in this region, these functions are not impaired.

2. Additional Disclosure of the Present Application

Figure 19:
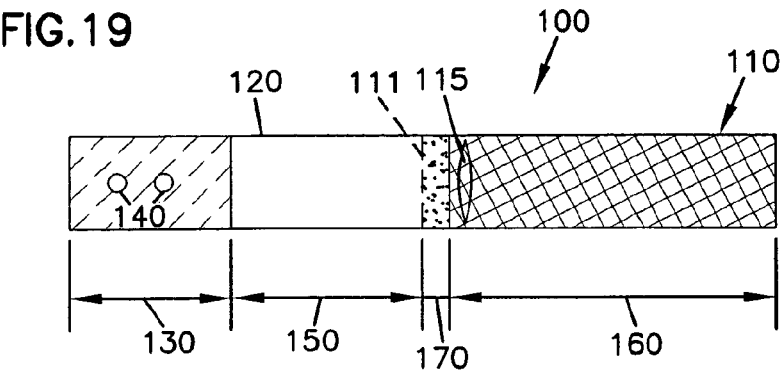
FIG. 19 is a side elevation view of a further alternative embodiment of an implant according to the present invention.
Figure 20:
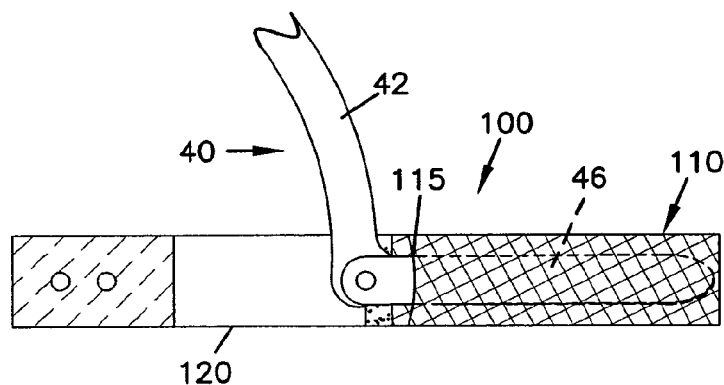
FIG. 20 is the view of FIG. 19 showing the tool of FIG. 5 in a closed position inserted within the implant of FIG. 19.
Figure 21:
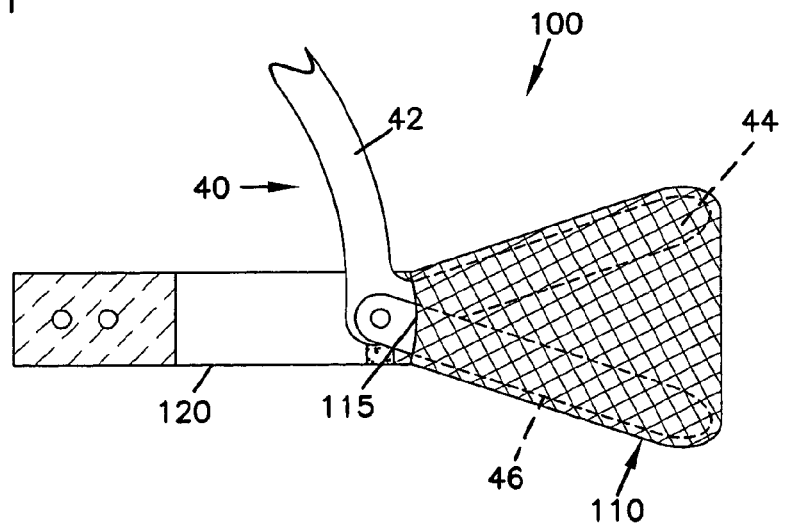
FIG. 21 is the view of FIG. 20 with the tool shown in an open position.

FIGS. 19-23 illustrate an alternative embodiment of the present invention. In FIGS. 19-23, an implant 100 includes a distal portion 110 and a proximal portion 120. The distal portion 110 is preferably a mesh construction such as a braid or knit which has interstitial spaces for promoting fibrosis and tissue ingrowth. The distal portion 110 is preferably constructed the same as implant 10 previously described. FIG. 19 shows the implant 100 with distal portion 110 in a collapsed state while FIG. 21 shows the distal portion 110 in a fully expanded state. The distal portion 110 includes a side slit 115 for receiving the blades 44, 46 of the previously described incision formation tool 40.

The proximal portion 120 is an elastomeric material such as silicone or the like. The silicone is molded over a first end 111 of the distal portion 110 to define an over-molded portion 170 (FIG. 19).

The silicone proximal portion 120 includes a most proximal reinforced region 130. Region 130 may have reinforcing fibers such as polyester to reinforce the strength of the silicone in the region 130. The region 130 includes a plurality of holes 140 spaced along the length of the region 130 for receiving an attachment screw 150 (shown only in FIG. 23). The silicone proximal portion 120 includes unreinforced region 150 so that the region 150 may elastically stretch for purposes that will become apparent. By way of non-limiting example, region 130 is about 1.5 cm in length, region 150 is about 2 cm and region 160 (the length of portion 110 not contained within silicone) is about 3 cm. (See FIG. 20).

Figure 22:
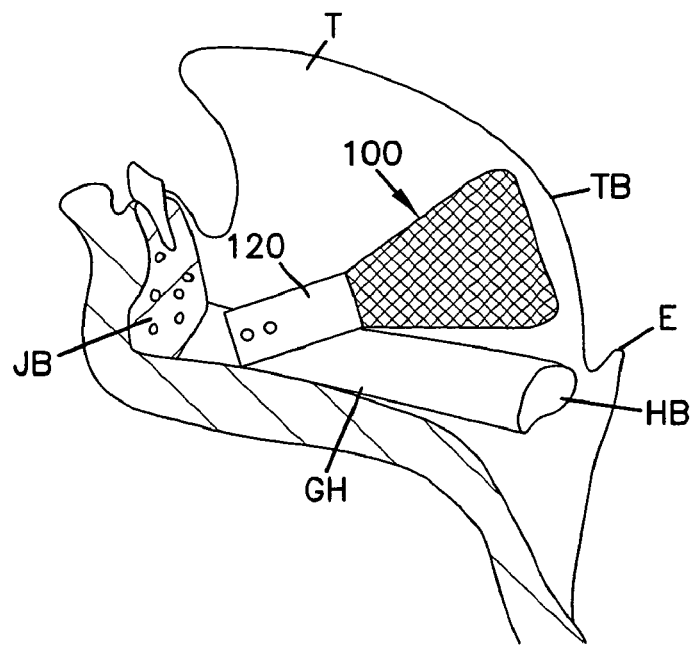
FIG. 22 is a side elevation schematic view of a portion of an upper airway of a patient showing the implant of FIG. 21 deployed within a tongue of a patient before attachment of the implant to a jaw bone of the patient.

In use of the implant 100, the incision formation tool 40 forms an incision within the tongue T as previously described. With the blades 44, 46 in the closed position, the blades are inserted through the slit 115 into the interior of the distal portion 110 as illustrated in FIG. 20. The combination is then inserted into the tongue T where the blades 44, 46 are moved to the open position causing the distal portion 110 to expand as illustrated in FIG. 21. FIG. 22 shows the expanded distal portion 110 within the tongue T following removal of the incision formation tool 40.

Figure 23:
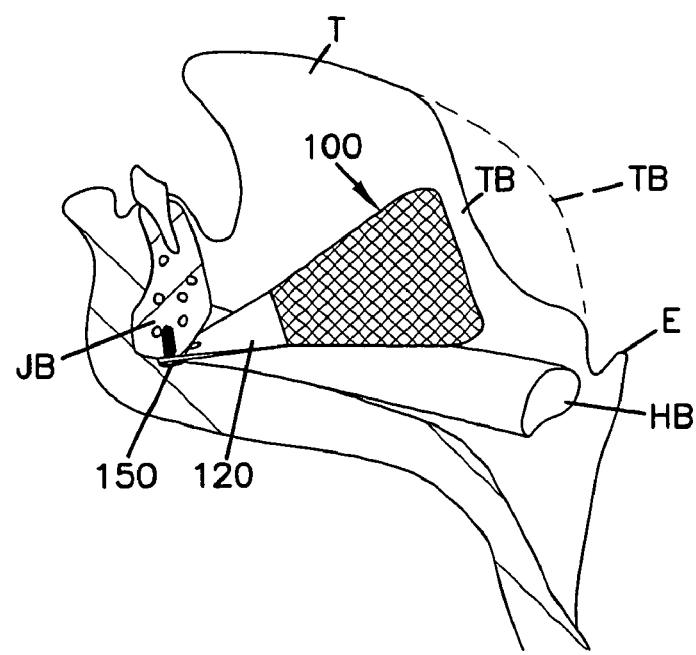
FIG. 23 is the view of FIG. 22 following attachment of the implant to the jaw bone.

After a period of time (for example, about 4 weeks), a healing process occurs and fibrosis results attaching the tissue of the tongue T to the mesh material of the distal portion 110. Following such healing, an incision (not shown) may be made into the tongue T from beneath the chin of the patient. The physician grabs the proximal portion 120 and retracts it relative to the base of the tongue TB. This causes a retraction of the tongue base TB from the pharyngeal wall. FIG. 23 illustrates this in an exaggerated manner with the original tongue base TB shown in phantom lines and the repositioned tongue base shown in solid lines TB.

With the tongue base TB so retracted, the proximal portion 120 is attached to the jaw bone JB by passing screw 150 through a select one of the holes 140 and into the jaw bone JB. The incision can then be closed with the apparatus 100 remaining in the position shown in FIG. 23.

During normal tongue functions such as speech and swallowing, the tongue T may be urged to move away from the jaw bone JB. This movement is facilitated by the elastic material of the proximal portion 120 so as not to interfere with normal speech and swallowing functions of the tongue.

It has been shown how the present invention has been obtained in a preferred embodiment. Modifications and equivalents of the disclosed concepts are intended to be included within the scope of the claims which are appended hereto.

What is claimed is:

1. A method for treating obstructive sleep apnea comprising:
    identifying a patient with sleep apnea attributable at least in part to movement of a base of a tongue of said patient toward a pharyngeal wall of said patient;
    identifying a region in the tongue extending from a mandibular-geniohyoid interface to the base of the tongue;
    stiffening a tissue of the tongue throughout the identified region;
    wherein said stiffening includes placing an implant of fibrosis-inducing material within the tongue with the implant and the fibrosis-inducing material of the implant extending throughout said entire region with the material selected to induce formation of fibrosis along said region; and
    attaching a proximal end of the implant to a jaw bone of the patient,
    wherein a proximal portion of the implant is elastomeric.

2. A method according to claim 1 wherein the identified region includes an area of the base of the tongue opposing the pharyngeal wall between an epiglottis and a trailing end of a soft palate.

3. A method according to claim 1 wherein the identified region includes an area of the base of the tongue between lateral extremities of the base of the tongue.

4. A method according to claim 1 wherein said implant is sized for said region to extend substantially between an epiglottis and a soft palate of the patient at the base of the tongue.

5. A method according to claim 4 wherein said implant is a substantially planar sheet when placed in the tongue with a narrow dimension extending transverse to the tongue, the proximal end of the implant being located within said region at said mandibular-geniohyoid interface, a distal end of the implant being located within the tongue at the base and extending between the epiglottis and the soft palate.

6. A method according to claim 1 wherein said implant is a tubular material selected to induce fibrosis formation, the proximal end of the implant being located at said mandibular-geniohyoid interface, a distal end of the implant being located at said base of the tongue.

7. A method according to claim 6 wherein said region includes an area of the base of the tongue between lateral extremities of the base of the tongue and said method includes placing multiples of said implants in a volume of said tongue within said region.

8. A method according to claim 1 wherein a material of said implant is selected for said implant to contract and expand with the tongue as the tongue heals.

9. A method according to claim 1 wherein the proximal end is attached to the jaw bone following a period of healing after placement of the implant in the tongue.

10. A method according to claim 1 wherein the elastomeric proximal portion expands and contracts with movement of the tongue in response to speech and swallowing.

11. A method according to claim 10 wherein the elastomeric proximal portion includes a reinforced region that facilitates attachment of the implant to the patient's jaw bone and an unreinforced region that permits the movement of the tongue.

12. A method for treating obstructive sleep apnea comprising:
  identifying a patient with sleep apnea attributable at least in part to movement of a base of a tongue of said patient toward a pharyngeal wall of said patient;
  identifying a region in the tongue extending from a mandibular-geniohyoid interface to the base of the tongue;
  stiffening a tissue of the tongue throughout the identified region;
  wherein said stiffening includes placing an implant of fibrosis-inducing material within the tongue with the implant extending within said region with the material selected to induce formation of fibrosis along said region; and
  attaching a proximal end of the implant to a jaw bone of the patient,
  wherein an elastomeric proximal portion of the implant includes a reinforced region that facilitates attachment of the implant to the patient's jaw bone and an unreinforced region that permits the movement of the tongue.

13. A method for treating obstructive sleep apnea comprising:
  identifying a patient with sleep apnea attributable at least in part to movement of a base of a tongue of said patient toward a pharyngeal wall of said patient;
  identifying a region in the tongue extending from a mandibular-geniohyoid interface to the base of the tongue;
  stiffening a tissue of the tongue throughout the identified region;
  wherein said stiffening includes placing an implant of fibrosis-inducing material within the tongue with the implant and the fibrosis-inducing material of the implant extending throughout said entire region with the material selected to induce formation of fibrosis along said region; and
  attaching a proximal end of the implant to a jaw bone of the patient,
  wherein a proximal portion of the implant is elastomeric, and
  wherein the proximal end is attached to the jaw bone following a period of healing after placement of the implant in the tongue.

14. An apparatus treating obstructive sleep apnea of a patient, said apparatus comprising:
  an implant sized to be placed within a tongue of the patient;
  the implant having a proximal portion and a distal portion;
  the distal portion sized to be implanted in the tongue near a base of the tongue;
  the distal portion selected of a material for creating a fibrotic response following implantation in the tongue;
  the proximal portion including a first end adapted to be secured to a jaw bone of the patient, wherein at least a portion of the proximal portion is elastomeric, the elastomeric proximal portion being selected to expand and contract with movement of the tongue in response to speech and swallowing,
  wherein the elastomeric proximal portion includes a reinforced region that facilitates attachment of the implant to the patient's jaw bone and an unreinforced region that permits the movement of the tongue.

15. An apparatus according to claim 14 wherein the distal portion is a material with interstitial spaces for tissue ingrowth.

16. An apparatus according to claim 15 wherein the material is a mesh.

* * * * *